(12) United States Patent
Hamilton et al.

(10) Patent No.: US 9,249,459 B2
(45) Date of Patent: *Feb. 2, 2016

(54) SINGLE CELL NUCLEIC ACID ANALYSIS

(71) Applicant: Fluidigm Corporation, South San Francisco, CA (US)

(72) Inventors: Amy Hamilton, San Francisco, CA (US); Min Lin, Foster City, CA (US); Alain Mir, Cupertino, CA (US); Martin Pieprzyk, Belmont, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,331

(22) Filed: Dec. 10, 2013

(65) Prior Publication Data

US 2014/0193812 A1 Jul. 10, 2014

Related U.S. Application Data

(63) Continuation of application No. 12/687,018, filed on Jan. 13, 2010, now Pat. No. 8,628,923.

(60) Provisional application No. 61/144,416, filed on Jan. 13, 2009, provisional application No. 61/146,583, filed on Jan. 22, 2009, provisional application No. 61/284,309, filed on Dec. 15, 2009.

(51) Int. Cl.
*C12Q 1/68* (2006.01)
*C12P 19/34* (2006.01)

(52) U.S. Cl.
CPC .............. *C12Q 1/686* (2013.01); *C12Q 1/6844* (2013.01); *C12Q 1/6881* (2013.01); *C12Q 2531/113* (2013.01); *C12Q 2531/119* (2013.01); *C12Q 2531/137* (2013.01); *C12Q 2565/101* (2013.01); *C12Q 2600/158* (2013.01); *C12Q 2600/178* (2013.01)

(58) Field of Classification Search
CPC .............................. C12Q 1/6844; C12Q 1/686
See application file for complete search history.

(56) References Cited

U.S. PATENT DOCUMENTS

| | | | |
|---|---|---|---|
| 6,045,993 A | 4/2000 | Mahony et al. | |
| 7,887,753 B2 | 2/2011 | Quake et al. | |
| 8,628,923 B2 * | 1/2014 | Hamilton et al. | 435/6.12 |
| 2002/0160404 A1 * | 10/2002 | Dietmaier et al. | 435/6 |
| 2003/0180715 A1 | 9/2003 | Kemp et al. | |
| 2003/0228613 A1 | 12/2003 | Bornarth et al. | |
| 2004/0110166 A1 | 6/2004 | Macevicz | |
| 2004/0229349 A1 | 11/2004 | Daridon | |
| 2005/0252773 A1 | 11/2005 | McBride et al. | |
| 2006/0053503 A1 | 3/2006 | Culiat et al. | |
| 2006/0141518 A1 | 6/2006 | Lao et al. | |
| 2008/0108063 A1 | 5/2008 | Lucero et al. | |
| 2008/0223721 A1 | 9/2008 | Cohen et al. | |
| 2009/0069194 A1 | 3/2009 | Ramakrishnan et al. | |
| 2009/0257920 A1 | 10/2009 | Facer et al. | |
| 2010/0178655 A1 | 7/2010 | Hamilton et al. | |
| 2010/0203538 A1 | 8/2010 | Dube et al. | |
| 2010/0273219 A1 | 10/2010 | May et al. | |
| 2011/0257039 A1 | 10/2011 | Wang et al. | |

FOREIGN PATENT DOCUMENTS

WO WO 2010/083250 7/2010

OTHER PUBLICATIONS

Wells et al. Detailed chromosomal and molecular genetic analysis of single cells by whole genome amplification and comparative genomic hybridisation. Nucleic Acids Res. (1999) vol. 27, No. 4, pp. 1214-1218.*
US Office Action dated Apr. 13, 2012 issued in U.S. Appl. No. 12/687,018.
US Final Office Action dated Mar. 1, 2013 issued in U.S. Appl. No. 12/687,018.
US Notice of Allowance dated Sep. 9, 2013 issued in U.S. Appl. No. 12/687,018.
PCT International Search Report and Written Opinion dated Sep. 16, 2010 issued in PCT/US2010/020942 [WO 2010/083250].
PCT International Preliminary Report on Patentability and Written Opinion dated Jul. 19, 2011 issued in PCT/US2010/020942 [WO 2010/083250].
Chinese Office Action dated Feb. 26, 2013 issued in 201080011426.7.
Chinese Second Office Action dated Nov. 15, 2013 issued in 201080011426.7.
Chinese Third Office Action dated May 13, 2014 issued in 201080011426.7.
Chinese Fourth Office Action dated Dec. 2, 2014 issued in 201080011426.7.
EA Office Action dated Mar. 29, 2013 issued in 201170933.
European Supplementary Search Report on Patentability and Written Opinion dated Apr. 26, 2012 issued in EP 10 73 2056.6.
European Office Action dated Apr. 7, 2014 issued in EP 10 732 056.6.
Israeli Office Action dated Nov. 14, 2013 issued in IL 214034.
Singapore Search Report and Written Opinion dated Feb. 26, 2013 issued in SG 201205203-1.
Singapore Search Report and Written Opinion dated Dec. 13, 2013 issued in SG 201205203-1.

(Continued)

*Primary Examiner* — Kenneth R. Horlick
*Assistant Examiner* — David Thomas
(74) *Attorney, Agent, or Firm* — Emily M. Haliday; Weaver Austin Villeneuve & Sampson LLP

(57) ABSTRACT

The present invention provides methods for analysis of genomic DNA and/or RNA from small samples or even single cells. Methods for analyzing genomic DNA can entail whole genome amplification (WGA), followed by preamplification and amplification of selected target nucleic acids. Methods for analyzing RNA can entail reverse transcription of the desired RNA, followed by preamplification and amplification of selected target nucleic acids.

35 Claims, 6 Drawing Sheets

(56) References Cited

OTHER PUBLICATIONS

Singapore Search Report and Written Opinion dated Nov. 6, 2014 issued in SG 201205203-1.

Ao et al. (1998) "Preimplantation genetic diagnosis of inherited cancer:Familial adenomatous polyposis coli" *Journal of Assisted Reproduction and Genetics* 15(3): 140-144.

Dietmaier et al. (1999) "Multiple mutation analyses in single tumor cells with improved whole genome amplification" *American Journal of Pathology* 154(1): 83-95.

Heinmoller et al. (2002) "Toward efficient analysis of mutations in single cells from ethanol-fixed, paraffin-embedded, and immunohistochemically stained tissues" *Laboratory Investigation* 82(4): 443-453.

Saitou et al., (Jan. 1, 2008) "Single-cell cDNA high-density oligonucleotide microarray analysis: detection of individual cell types and properties in complex biological processes", *Reproductive Biomedicine Online, Reproductive Healthcare LTD. GB*, 16(1):26-40.

Snabes et al. (1994) "Preimplantation Single-Cell Analysis of Multiple Genetic Loci by Whole-Genome Amplification" *Proceedings of the National Academy of Sciences of USA* 91(13): 6181-6185.

Wells et al. (1999) "Detailed chron1osomal and molecular genetic analysis of single cells by whole genome amplification and comparative genomic hybridisation" *Nucleic Acids* Research 27(4): 1214-18.

Israeli Office Action dated Feb. 1, 2015 issued in IL 214034.

Kurimoto et al., (2006) "An improved single-cell cDNA amplification method for efficient high-density oligonucleotide microarray analysis," Nucleic Acids Research, 34(5):e42, 17pp.

\* cited by examiner

SINGLE CELL NUCLEIC ACID ANALYSIS

CROSS-REFERENCE TO RELATED APPLICATIONS

This application is a continuation of U.S. non-provisional application Ser. No. 12/687,018, filed Jan. 13, 2010, which claims the benefit of U.S. provisional application No. 61/144,416, filed Jan. 13, 2009; U.S. provisional application No. 61/146,583, filed Jan. 22, 2009; and U.S. provisional application No. 61/284,309, filed Dec. 15, 2009, all of which are hereby incorporated by reference in their entireties.

FIELD OF THE INVENTION

The invention relates to methods useful for analyzing the nucleic acids, e.g., genomic DNA or RNA (e.g., non-coding RNA or mRNA), of small populations of cells or single cells.

BACKGROUND OF THE INVENTION

An obstacle to the rapid and reliable analysis of genomic DNA or RNA (e.g., non-coding RNA or mRNA) from small samples or single cells has been that the reproducibility of conventional polymerase chain reaction (PCR) has been inadequate to ensure that all target nucleic acids of interest are amplified sufficiently to be detected.

SUMMARY OF THE INVENTION

In certain embodiments, the invention provides methods of analyzing nucleic acids from a single cell. In particular embodiments, the single cell is a mammalian cell, such as, for example, a cell from a preimplantation embryo, a stem cell, a suspected cancer cell, a cell from a pathogenic organism, and/or a cell obtained from a crime scene. In illustrative embodiments, the cell is a human blastomere (e.g., from an eight-cell stage embryo) or a human stem cell.

For example, an illustrative method for genotyping a single cell entails:
(a) performing whole genome amplification of the genome of a single cell to produce an amplified genome;
(b) preamplifying the amplified genome to produce a preamplification reaction mixture comprising one or more amplicons specific for one or more target nucleic acids (loci); and
(c) amplifying and detecting the one or more amplicons.

In certain embodiments, whole genome amplification (WGA) is carried out such that a reaction plateau is not reached. Typically, WGA is performed for more than two amplification cycles and, in particular embodiments, fewer than about 10 cycles (e.g., between about four and eight cycles, inclusive).

Suitable WGA techniques include primer extension PCR (PEP), degenerated oligonucleotide primed PCR, ligation-mediated PCR (LMP), the T7-based linear amplification of DNA (TLAD), and multiple displacement amplification (MDA).

An illustrative method for analyzing the RNA from a single cell entails:
(a) preparing DNA from the RNA from a single cell;
(b) preamplifying the DNA to produce a preamplification reaction mixture comprising one or more amplicons specific for one or more target nucleic acids (target RNA(s)); and
(c) amplifying and detecting the one or more amplicons.

In particular embodiments, cDNA is produced by reverse transcription or amplification of mRNA. In other embodiments, DNA is produced by reverse transcription or amplification of non-coding RNA. For example, the non-coding RNA can be small nucleolar RNA (snoRNA), microRNA (miRNA), small interfering RNA (siRNA), and/or Piwi-interacting RNAs (piRNA).

The nucleic acids generated, e.g., from a single cell's genomic DNA or RNA, can be subjected to preamplification. When DNA is produced from RNA, e.g., by reverse transcription, preamplification can then be carried out in the same reaction mixture. In certain embodiments, preamplification is carried out using one or more primer pairs specific for or more target nucleic acids (e.g., loci) of interest. Preamplification can, in specific embodiments, be carried out for 8-18 cycles. In particular embodiments, no probe is present in the preamplification mixture.

Amplicons produced by preamplification can be detected, in certain embodiments, by further amplification. In particular embodiments, this further amplification is carried out using one or more primer pairs specific one or more target nucleic acids (loci) of interest. These primer pairs can be the same as, or different from, those used for preamplification.

In illustrative embodiments, the preamplification can be carried out, and the resulting preamplification mixture can be distributed into separate chambers of a microfluidic device prior to amplication. Suitable microfluidic devices include those fabricated, at least in part, from an elastomeric material.

In certain embodiments, the preamplification and/or the amplification is carried out by polymerase chain reaction (PCR). When the amplification is carried out by PCR, the presence of an amplification product can be determined by quantitative real-time polymerase chain reaction (qPCR). In such embodiments, a universal qPCR probe, such as e.g., a double-stranded DNA (dsDNA) dye, can employed in the amplification mixtures to detect amplification products. Alternatively, or additionally, one or more target-specific qPCR probes can be employed to detect amplification products. In illustrative embodiments, the presence of an amplification product is detected using a fluorogenic nuclease assay. For example, the presence of an amplification product can be detected using a dual-labeled fluorogenic oligonucleotide probe.

Primer pairs used in preamplification and/or amplification can amplify single nucleotide polymorphisms (SNPs). In particular embodiments, these can be correlated with the presence of one or more genetic defects.

DETAILED DESCRIPTION

Figure 1:
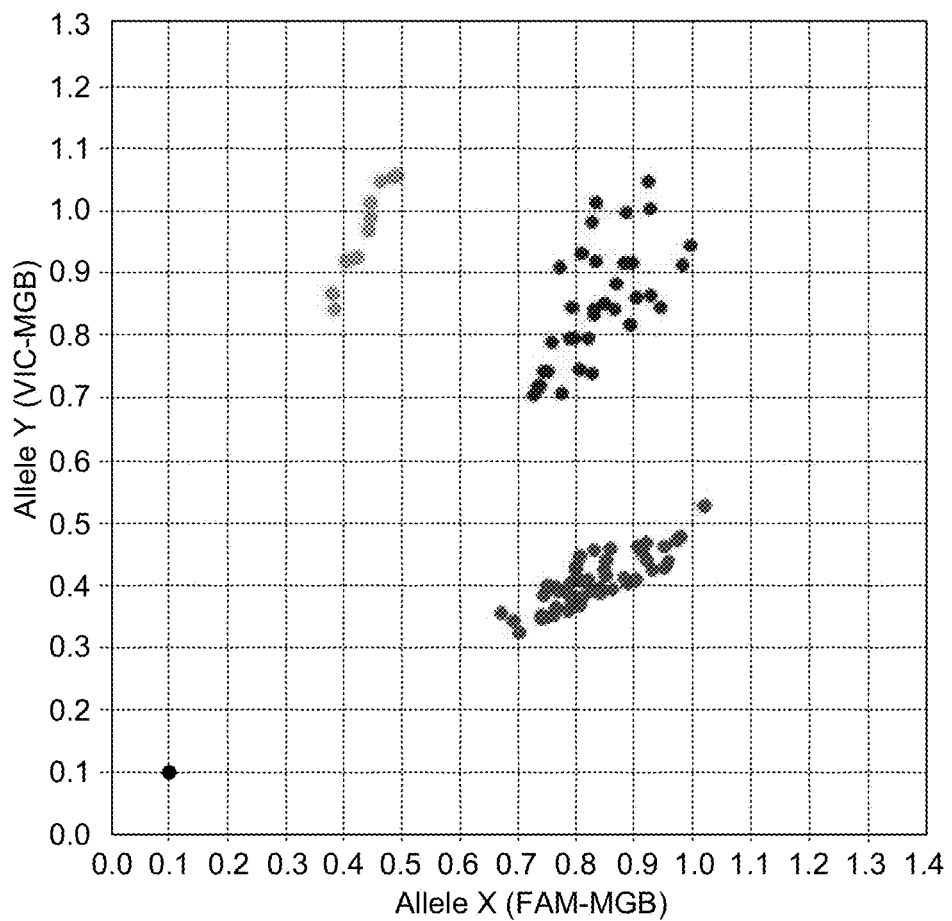
FIG. 1: A BioMark Genotyping Analysis software SNP genotyping cluster plot of up to 94 individual cells.
Figure 2:
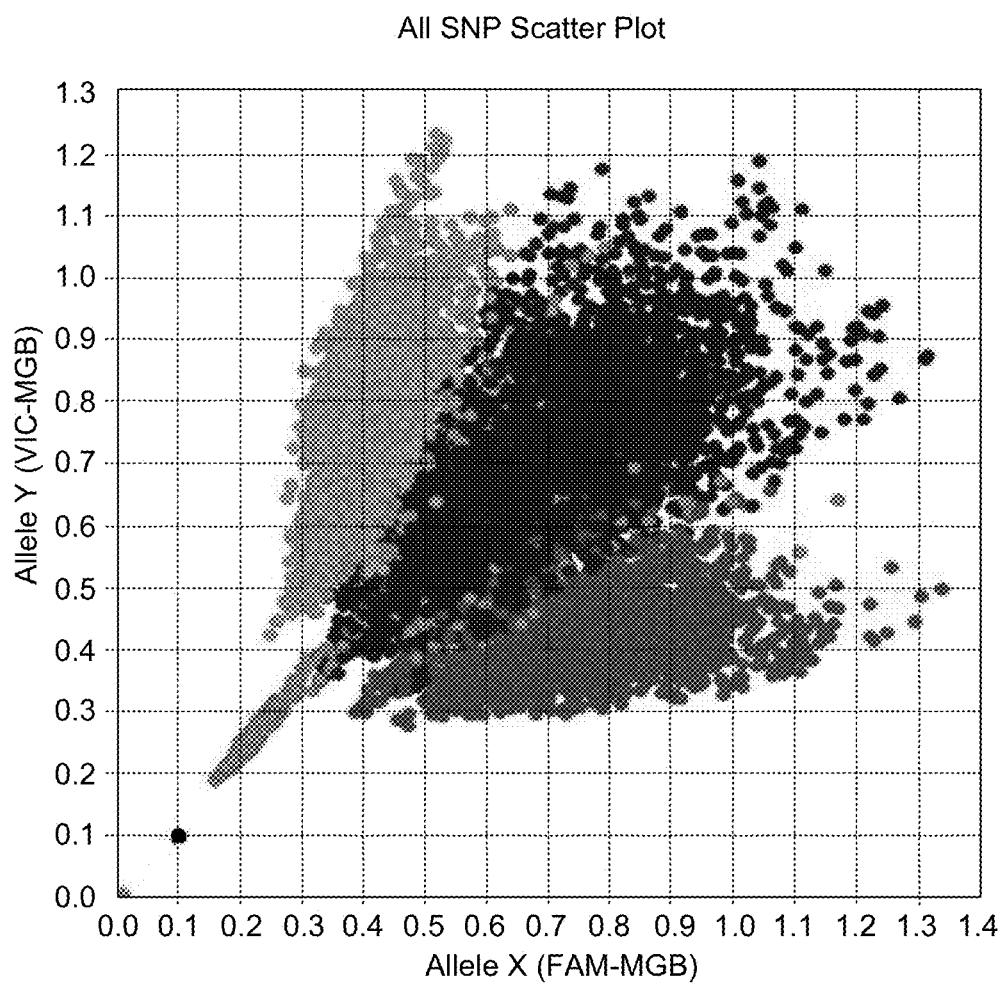
FIG. 2: An All SNP cluster plot from BioMark Genotyping Analysis software of 96 unique SNP TaqMan assays against 94 single cells.

The ability to analyze the nucleic acids, e.g., the genomic DNA, of small samples is important, for example, in assessing samples in connection with in vitro fertilization (IVF), CTC, and studies of tumor uniformity. The genotype of single cells is of interest in a variety of contexts, including developmental biology, detection of mutations, and bacteriology. The expression patterns of coding RNA (mRNA) and non-coding RNA are similarly of interest, for example, in understanding the molecular basis of differentiation, development, disease, and cellular responses to various stimuli.

In certain embodiments, the present invention includes methods based on the use of whole genome amplification (WGA), followed by preamplification and amplification of selected target nucleic acids. The use of WGA provides multiple copies of the genome before the preamplification step, increasing the likelihood of complete preamplification of all target nucleic acids of interest. In other embodiments, a DNA representation of RNA is produced, e.g., cDNA produced from mRNA, followed by preamplification and amplification of selected target nucleic acids.

Definitions

Terms used in the claims and specification are defined as set forth below unless otherwise specified.

The term "nucleic acid" refers to a nucleotide polymer, and unless otherwise limited, includes known analogs of natural nucleotides that can function (e.g., hybridize) in a similar manner to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acid, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases, phosphodiester bonds, or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods described herein. Target nucleic acids include, for example, loci of interest (e.g., single nucleotide polymorphisms) in genotyping studies, mRNAs of interest in expression studies, as well as non-coding RNAs. Target nucleic acids that are originally (i.e., prior to experimental intervention) found in the form of RNA are also termed "target RNAs" herein.

Non-coding RNAs include those RNA species that are not necessarily translated into protein. These include, but are not limited to, transfer RNA (tRNA) and ribosomal RNA (rRNA), as well as RNAs such as small nucleolar RNAs (snoRNA; e.g., those associated with methylation or pseudouridylation), microRNAs (miRNA; which regulate gene expression), small interfering RNAs (siRNAs; which are involved in the RNA interference (RNAi) pathway, where they interfere with the expression of specific genes, but have also been shown to act as antiviral agents and in shaping the chromatin structure of a genome) and Piwi-interacting RNAs (piRNAs; which form RNA-protein complexes through interactions with Piwi proteins; these piRNA complexes have been linked to transcriptional gene silencing of retrotransposons and other genetic elements in germ line cells, particularly those in spermatogenesis), and long non-coding RNAs (long ncRNAs; which are non-coding transcripts that are typically longer than about 200 nucleotides).

As used herein the term "target nucleotide sequence" refers to a molecule that has the nucleotide sequence of a target nucleic acid, such, for example, the amplification product obtained by amplifying a target nucleic acid or the cDNA produced upon reverse transcription of an mRNA target nucleic acid.

As used herein, the term "complementary" refers to the capacity for pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity (Watson-Crick or non-canonical pairing) between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands and the consequent stacking interactions.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL.152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m = 81.5 + 0.41(\% \text{ G}+\text{C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules, but double-stranded oligonucleotides can also be produced.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 6 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer can include a nucleotide tag, e.g., appended to its 5' end. The term "nucleotide tag" is used herein to refer to a predetermined nucleotide sequence that is added to a target nucleotide sequence. The nucleotide tag can encode an item of information about the target nucleotide sequence, such the identity of the target nucleotide sequence, the chromosome from which that sequence derives, or the identity of the sample from which the target nucleotide sequence was derived. Nucleotide tag sequences are generally not used as primer binding sites in the first round of amplification.

A primer is said to anneal to another nucleic acid if the primer, or a portion thereof, specifically hybridizes to a nucleotide sequence within the nucleic acid. The statement that a primer hybridizes to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A primer pair is said to be "unique" if it can be employed to specifically amplify a particular target nucleotide sequence in a given amplification mixture.

A "probe" is a nucleic acid capable of binding to a target nucleic acid of complementary sequence through one or more types of chemical bonds, generally through complementary base pairing, usually through hydrogen bond formation (but also through co-ordinal metal complexes), thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 6 to 15 nucleotides in length. Other probes are at least 20, 30, or 40 nucleotides long. Still other probes are somewhat longer, being at least 50, 60, 70, 80, or 90 nucleotides long. Yet other probes are longer still and are at least 100, 150, 200 or more nucleotides long. Probes can also be of any length that is within any range bounded by any of the above values (e.g., 15-20 nucleotides in length). Primers can also function as probes.

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal most specifically to the target sequence under stringent hybridization conditions.

Amplification according to the present teachings encompasses any means by which at least a part of at least one target nucleic acid is copied, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February;4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February;13(2):294-307, and Landegren et al., Science 241:1077-80 (1988), Demidov, V., Expert Rev Mol Diagn. 2002 November;2(6):542-8., Cook et al., J Microbiol Methods. 2003 May;53(2):165-74, Schweitzer et al., Curr Opin Biotechnol. 2001 February;12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

Thus, as used herein, the term amplification includes isothermal amplification methods. Isothermal amplification uses a constant temperature rather than cycling through denaturation and annealing/extension steps. Some means of strand separation, e.g., an ezyme, is used in place of thermal denaturation. Examples of isothermal amplification include: hyperbranched strand displacement amplification (Groathouse, N., et al. (2006) "Isothermal Amplification and Molecular Typing of the Obligate Intracellular Pathogen Mycobacterium leprae Isolated from Tissues of Unknown Origins" J. Clin. Micro. 44 (4): 1502-1508); helicase-dependent amplification (Vincent, M., et al. (2004) "Helicase-dependent isothermal DNA amplification" EMBO Rep. 5 (8): 795-800); multiple displacement amplification (MDA; Luthra, R., and Medeiros, J. (2004) "Isothermal Multiple Displacement Amplification" J Mol Diagn. 6 (3): 236-242); loop-mediated isothermal amplification (Notomi, T., et al. (2000) Nucleic Acids Research 28 (1); PAN-AC (David, F. and Turlotte, E., (1998) "An Isothermal Amplification Method" C.R.Acad. Sci Paris, Life Science 321 (1): 909-14); strand displacement amplification (SDA; Nycz, C., et al. (1998) Analytical Biochemistry 259 (2): 226-234); rolling circle amplification (RCA; Lizardi, P., et al., (1998)"Mutation detection and single-molecule counting using isothermal rolling-circle amplification" Nature Genetics 19: 225-232); nucleic acid strand-based amplification (NASBA; Van Der Vliet, G., et al. (1993) "Nucleic acid sequence-based amplification (NASBA) for the identification of mycobacteria" Journal of General Microbiology 139 (10): 2423-2429; and recombinase polymerase amplification (U.S. Pat. Nos. 7,485,428; 7,399,590; 7,270,981; and 7,270,951, each of which is incorporated by reference in its entirety and specifically for its description of recombinase polymerase amplification).

The term "qPCR" is used herein to refer to quantitative real-time polymerase chain reaction (PCR), which is also known as "real-time PCR" or "kinetic polymerase chain reaction."

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, nucleotides, labels, dyes, nucleases, and the like. Reagents for enzyme reactions include, for example, enzymes, substrates, cofactors, buffer, metal ions, inhibitors, and activators.

The term "universal detection probe" is used herein to refer to any probe that identifies the presence of an amplification product, regardless of the identity of the target nucleotide sequence present in the product.

The term "universal qPCR probe" is used herein to refer to any such probe that identifies the presence of an amplification product during qPCR. In certain embodiments, one or more amplification primers can comprise a nucleotide sequence to which a detection probe, such as a universal qPCR probe binds. In this manner, one, two, or more probe binding sites can be added to an amplification product during the amplification step of the methods described herein. Those of skill in the art recognize that the possibility of introducing multiple probe binding sites during preamplification (if carried out) and amplification facilitates multiplex detection, wherein two or more different amplification products can be detected in a given amplification mixture or aliquot thereof The term "universal detection probe" is also intended to encompass primers labeled with a detectable label (e.g., a fluorescent label), as well as non-sequence-specific probes, such as DNA binding dyes, including double-stranded DNA (dsDNA) dyes, such as SYBR Green.

The term "target-specific qPCR probe" is used herein to refer to a qPCR probe that identifies the presence of an amplification product during qPCR, based on hybridization of the qPCR probe to a target nucleotide sequence present in the product.

"Hydrolysis probes" are generally described in U.S. Pat. No. 5,210,015, which is incorporated herein by reference in its entirety for its description of hydrolysis probes. Hydrolysis probes take advantage of the 5'-nuclease activity present in the thermostable Taq polymerase enzyme typically used in the PCR reaction (TAQMAN® probe technology, Applied Biosystems, Foster City, Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, hydrolysis probes suitable for use in the methods described herein can be capable of detecting 8-mer or 9-mer motifs that are common in the human and other genomes and/or transcriptomes and can have a high $T_m$ of about 70° C. enabled by the use of linked nucleic acid (LNA) analogs.

The term "label," as used herein, refers to any atom, moiety, or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 300 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

A "polymorphic marker" or "polymorphic site" is a locus at which nucleotide sequence variance occurs. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

A "locked nucleic acid," often referred to as inaccessible RNA, is a modified RNA nucleotide. The ribose moiety of a locked nucleic acid nucleotide is modified with an extra bridge connecting the 2' and 4' carbons. The bridge "locks" the ribose in the 3'-endo structural conformation, which is often found in the A-form of DNA or RNA. Locked nucleic acid nucleotides can be mixed with DNA or RNA bases in the oligonucleotide whenever desired. The locked ribose conformation enhances base stacking and backbone pre-organization. This significantly increases the thermal stability (melting temperature) of oligonucleotides. See, e.g., Kaur, H; Arora, A; Wengel, J; Maiti, S (2006). "Thermodynamic, Counterion, and Hydration Effects for the Incorporation of Locked Nucleic Acid Nucleotides into DNA Duplexes," Biochemistry 45 (23): 7347-55.

Methods of Analyzing Nucleic Acids from Small Populations or Single Cells

Samples/Cells Suitable for Analysis

Samples containing nucleic acids or single cells can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, e.g., mammals, and particularly humans. Suitable nucleic acids can also be obtained from an environmental source (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Cells may either be cultured or from primary isolates such as clinical samples. Illustrative samples include samples of plasma, serum, spinal fluid, lymph fluid, peritoneal fluid, pleural fluid, oral fluid, and external sections of the skin; samples from the respiratory, intestinal, genital, and urinary tracts; samples of tears, saliva, blood cells, stem cells, or tumors. For example, samples of fetal DNA can be obtained from an embryo (e.g., from one or a few embryonic or fetal cells) or from maternal blood. Samples can be obtained from live or dead organisms or from in vitro cultures. Illustrative samples can include single cells, paraffin-embedded tissue samples, and needle biopsies. Nucleic acids useful in the methods described herein can also be derived from one or more nucleic acid libraries, including cDNA, cosmid, YAC, BAC, P1, PAC libraries, and the like.

Samples may reflect particular states, e.g., cell proliferation, cell differentiation, cell death, disease, exposure to stimuli, and/or stages, e.g., stages of development.

In particular embodiments, the methods described herein can carried out on a single cell from a preimplantation embryo, a stem cell, a suspected cancer cell, a cell from a pathogenic organism, and/or a cell obtained from a crime scene. For example, a human blastomere (e.g., from an eight-cell stage embryo or later) can be analyzed to determine whether the genome includes one or more genetic defects.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods described herein to be performed. Where the target nucleic acids are mRNA, the RNA can be reversed transcribed into cDNA by standard methods known in the art and as described in Sambrook, J., Fritsch, E. F., and Maniatis, T., Molecular Cloning: A Laboratory Manual. Cold Spring Harbor Laboratory Press, NY, Vol. 1, 2, 3 (1989), for example. The cDNA can then be analyzed according to the methods described herein.

In certain embodiments, a single cell can be added directly to a suitable WGA reaction mixture and WGA carried out. In other embodiments, the RNA of a single cell can be converted to DNA (e.g., cDNA) or the RNA directly amplified.

Target Nucleic Acids

Any target nucleic acid that can be amplified can be detected using the methods described herein. In some embodiments, at least some nucleotide sequence will be known for the target nucleic acids. For example, if PCR is used for preamplification/amplification of target nucleic acids, sufficient sequence information is typically available for each end of a given target nucleic acid to permit design of suitable amplification primers, although, those of skill in the art appreciate that target nucleic acids of unknown sequence can be amplified (e.g., using a pool of degenerate primers or a pool of combinatorial primers, such as random hexamers) as can mRNA (e.g., using oligo-dT).

The targets can include, for example, nucleic acids associated with pathogens, such as viruses, bacteria, protozoa, or fungi; RNAs, e.g., those for which over-or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, and/or mutated) in genetic diseases or other pathologies; sequences that are associated with desirable or undesirable traits; and/or sequences that uniquely identify an individual (e.g., in forensic or paternity determinations).

In particular embodiments, the target nucleic acids include polymorphisms, such as single nucleotide polymorphisms (SNPs). In this case, the amplification primers can be SNP-specific, meaning that at least one primer hybridizes to a SNP, such that an amplicon is produced only if the SNP is present in the sample nucleic acids.

In certain embodiments, it may be desirable to amplify a collection of target nucleic acids, e.g., a collection of SNPs, mRNAs, non-coding RNAs (e.g., miRNAs) for the purpose of characterizing particular states, e.g., cell proliferation, cell differentiation, cell death, disease, exposure to stimuli, and/or stages, e.g., stages of development. For example, a collection of target nucleic acids, such as miRNAs can be amplified and analyzed for correlations with particular patterns of gene expression.

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. Primers can also bear nucleotide tags (which are not necessarily intended to bind to target nucleic acids) e.g., in an initial amplification (such as a preamplification). One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) *Meth. Mol. Biol.,* 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458, 066 and the like, or can be provided from a commercial source. Alternatively, RNA primers can be derived by cleavage of double-stranded RNA with RNAase III.

Primers may be purified by using a Sephadex column (Amersham Biosciences, Inc., Piscataway, N.J.) or other methods known to those skilled in the art. Primer purification may improve the sensitivity of the methods of described herein.

Analysis of Genomic DNA—Whole Genome Amplification

To analyze genomic DNA, the sample nucleic acids can be amplified using a whole genome amplification (WGA) procedure. Suitable WGA procedures include:

Primer extension PCR (PEP) and improved PEP (I-PEP)—PEP typically uses Taq polymerase and 15-base random primers that anneal at a low stringency temperature. The use of Taq polymerase implies that the maximal product length is about 3 kb.

Degenerated oligonucleotide primed PCR (DOP-PCR)—DOP-PCR is well-established, widely accepted, and technically straightforward method. DOP-PCR uses Taq polymerase and semi-degenerate oligonucleotides (CGACTCGAGNNNNNNATGTGG; SEQ ID NO:1) that bind at a low annealing temperature at approximately one million sites in the human genome. The first cycles are followed by a large number of cycles with a higher annealing temperature, allowing only for the amplification of the fragments that were tagged in the first step. DOP-PCR generates, like PEP, fragments that are in average 400-500 bp, with a maximum size of 3 kb, although a DOP-PCR method that was able to produce fragments up to 10 kb had been described.

Ligation-mediated PCR (LMP)—LMP uses endonuclease or chemical cleavage to fragment the genomic DNA sample and linkers and primers for its amplification. It was first described by Ludecke and coworkers and was later adapted for the WGA of small quantities of gDNA and single cells. Rubicon Genomics commercialises different kits (Omniplex) that allow for the amplification of RNA, DNA and methylated DNA sequences. Advantages include that the method is able to amplify degraded DNA and that all steps are performed in the same tube. A limitation is that it generates fragments only up to 2 kb.

T7-based linear amplification of DNA (TLAD)—TLAD is a variant on the protocol originally designed by to amplify mRNA, that has been adapted for WGA. It uses Alu I restriction endonuclease digestion and a terminal transferase to add a polyT tail on the 3' terminus. A primer is then used with a 5' T7 promoter and a 3' polyA tract, and Taq polymerase is used to synthesise the second strand. Then the sample is submitted to in vitro transcription reaction and posterior reverse transcription. A major advantage is that TLAD does not introduce sequence and length-dependent biases.

Multiple displacement amplification (MDA)—MDA is a non-PCR-based isothermal method based on the annealing of random hexamers to denatured DNA, followed by strand-displacement synthesis at constant temperature. It has been applied to small genomic DNA samples, leading to the synthesis of high molecular weight DNA with limited sequence representation bias. As DNA is synthesized by strand displacement, a gradually increasing number of priming events occur, forming a network of hyper-branched DNA structures. The reaction can be catalysed by the Phi29 DNA polymerase or by the large fragment of the Bst DNA polymerase. The Phi29 DNA polymerase possesses a strand displacement activity and a proofreading activity resulting in error rates 100 times lower than the Taq polymerase.

Kits for WGA are available commercially from, e.g., Qiagen, Inc. (Valencia, Calif. USA), Sigma-Aldrich (Rubicon Genomics; e.g., Sigma GenomePlex® Single Cell Whole Genome Amplification Kit, PN WGA4-50RXN). The WGA step of the methods described herein can be carried out using any of the available kits according to the manufacturer's instructions.

In particular embodiments, the WGA step is limited WGA, i.e., WGA is stopped before a reaction plateau is reached. Typically, WGA is performed for more than two amplification cycles. In certain embodiments, WGA is performed for fewer than about 10 amplification cycles, e.g., between four and eight cycles, inclusive. However, WGA can be performed for 3, 4, 5, 6, 7, 8, or 9 cycles or for a number of cycles falling within a range defined by any of these values.

Analysis of RNA

In certain embodiments, RNA from single cell or a small population of cells can be analyzed for one or more RNA targets. Suitable RNA targets include mRNA, as well as non-coding RNA, such as small nucleolar RNA (snoRNA), microRNA (miRNA), small interfering RNA (siRNA), and Piwi-interacting RNAs (piRNA). In particular embodiments, the RNA of interest is converted to DNA, e.g., by reverse transcription or amplification.

For example, to analyze mRNA of a single cell or a small population of cells, the mRNA is generally converted to a DNA representation of the mRNA population. In certain embodiments, the method(s) employed preferably yield(s) a population of cDNAs, wherein the relative amounts of each cDNA is approximately the same as the relative amounts of the corresponding mRNAs in the sample population.

In particular embodiments, reverse transcription can be employed to produce cDNA from the mRNA template, utilizing reverse transcriptase according to standard techniques. This enzyme, which is present in all retroviruses (e.g., avian myeloblastoma virus), adds deoxyribonucleotides to the 3' terminus of a primer (Varmus, Science 240: 1427-1435 (1988)). Reverse transcription of a cell's mRNA population can be primed, e.g., with the use of specific primers, oligo-dT, or random primers. To synthesize a cDNA library representative of cellular mRNA, a first strand of cDNA complementary to the sample cellular RNA can be synthesized using reverse transcriptase. This can be done using the commercially available BRL Superscript II kit (BRL, Gaithersburg, Md.) or any other commercially available kit. Reverse transcriptase preferentially utilizes RNA as a template, but can also utilize single-stranded DNA templates. Accordingly, second strand cDNA synthesis can be carried out using reverse transcriptase and suitable primers (e.g., poly-A, random primers, etc.). Second strand synthesis can also be carried out using E. coli DNA polymerase I. The RNA can be removed at the same time the second cDNA strand is synthesized or afterwards. This is done by, for example, treating the mixture to an RNase such as E. coli RNase H, that degrades the RNA. As noted above, Rubicon Genomics sells kits (Omniplex) that allow for the amplification of RNA.

In other embodiments, an amplification method is employed to produce cDNA from the mRNA template. In such embodiments, an amplification method that produces a population of cDNA that is representative of the mRNA population is typically employed.

The analysis of non-coding RNA from a single cell or a small population of cells also typically begins with the conversion of the RNA of interest to DNA. This conversion can be carried out by reverse transcription or amplification. In certain embodiments, the method(s) employed preferably yield(s) a population of DNAs, wherein the relative amounts of each DNA is approximately the same as the relative amounts of the corresponding mRNAs in the sample population. The target RNAs can be selectively reverse-transcribed or amplified using primers that anneal preferentially to the RNAs of interest. Suitable primers are commercially available or can be designed by those of skill in the art. For example, Applied Biosystems sells MegaPlex™ Pools of primers for microRNA (miRNA) targets. These primers can be used for both reverse transcription (RT) and specific target amplification (STA). See, e.g., Example 2B.

Preamplification

In particular embodiments, the amplified genome produced by WGA or the DNA produced from RNA (e.g., cDNA) is preamplified to produce a preamplification reaction mixture that includes one or more amplicons specific for one or more target nucleic acids of interest. In certain embodiments, preamplification is carried out using one or more primer pairs specific for the one or more target nucleic acids of interest. Preamplification is typically carried out using preamplification primers, a suitable buffer system, nucleotides, and DNA polymerase enzyme (e.g., a polymerase enzyme modified for "hot start" conditions). The amplicons prepared by the method can then be further subjected to PCR analysis either in an endpoint assay or a real-time assay.

An exemplary reaction mixture for preamplification contains an appropriate buffer, a source of magnesium ions ($Mg^{2+}$) in the range of about 1 to about 10 mM, preferably in the range of about 2 to about 8 mM, nucleotides, and optionally, detergents, and stabilizers. An example of one suitable buffer is TRIS buffer at a concentration of about 5 mM to about 85 mM, with a concentration of 10 mM to 30 mM preferred. In one embodiment, the TRIS buffer concentration is 20 mM in the reaction mix double strength (2×) form. The reaction mix can have a pH range of from about 7.5 to about 9.0, with a pH range of about 8.0 to about 8.5 as typical. Concentration of nucleotides can be in the range of about 25 mM to about 1000 mM, typically in the range of about 100 mM to about 800 mM. Examples of dNTP concentrations are 100, 200, 300, 400, 500, 600, 700, and 800 mM. Detergents such as Tween 20, Triton X 100, and Nonidet P40 may also be included in the reaction mixture. Stabilizing agents such as dithiothreitol (DTT, Cleland's reagent) or mercaptoethanol may also be included.

In particular embodiments, the preamplification primers are the same sequence as those to be used in the amplification assays for which the sample is being prepared although generally in reduced concentration. The primer concentration can, e.g, be about 10 to about 250 times less than the primer concentrations used in the amplification assay. Embodiments include the use of primers that are about 10, 20, 35, 50, 65, 75, 100, 125, 150, 175, and 200 times less than that of the primer concentration in the amplification assay. Primers used in the preamplification can include random primers, poly A tails, and/or specific primers designed to amplify the target nucleic acids of interest. The reaction mix can optionally contain a reference dye for normalizing subsequent real quantitative PCR analysis results. An example of a common commercially available reference dye is ROX. A commercially available reaction mix containing ROX dye is CellsDirect 2X Reaction Mix, Cat. Nos. 11754-100 and 11754-500, available from Invitrogen Corporation.

A Taq polymerase enzyme is also added to the reaction mix. Platinum® Taq DNA is a recombinant Taq DNA polymerase complexed with an antibody that inhibits polymerase activity at ambient temperatures. Full polymerase activity is restored after the denaturation step in PCR, providing a "hot start."

In specific embodiments, preamplification is carried out for at least two cycles. In certain embodiments, preamplification is carried out for fewer than about 20 cycles, e.g., between 8 and 18 cycles, inclusive. However, preamplification can be performed for 3, 4, 5, 6, 7, 8, 9, 10, 11, 12, 13, 14, 15, 16, 17, 18, 19, 20, 21, 22, 23, or 24 cycles or for a number of cycles falling within a range defined by any of these values. In an exemplary embodiment, preamplification is carried out for about 14 cycles in order to increase the amplicons to be detected by about 16,000 fold.

Amplification

The amplicons produced upon preamplification are conveniently analyzed by an amplification method, such as PCR. In particular embodiments, a preamplified sample from a single cell or small cell population may be used for many separate PCR reactions performed in a low-volume PCR reaction apparatus. In certain embodiments, preamplification is carried out using one or more primer pairs specific for the one or more target nucleic acids of interest. Thus, a low-volume PCR reaction apparatus can include separate reaction chambers for amplifying with each primer pair, such that the production of an amplicon in a particular reaction chamber indicates that the corresponding target nucleic acid was present in the sample.

The reaction chambers for running low-volume PCR may be from about 2 nL to about 500 nL. The lower the reaction chamber volume, the greater the number of individual assays that may be run (either using different probe and primer sets or as replicates of the same probe and primer sets or any permutation of numbers of replicates and numbers of different assays). In one embodiment, the reaction chamber is from about 2 nL to about 50 nL, preferably 2 nL to about 25 nL, more preferably from about 4 nL to about 15 nL. In some embodiments, the reaction chamber volume is 5 nL, 6, nL, 7 nL, 8 nL, 9 nL, 10 nL, 11 nL, or 12 nL.

The reaction chambers may be constructed of an non-reactive material, such as glass, plastic, silicon, elastomeric polymers such as polydimethylsiloxane, polyurethane, or other polymers.

In particular embodiments, the products of preamplification are analyzed using the BioMark™ system (Fluidigm Corporation, South San Francisco, Calif.). The BioMark system uses a polydimethylsiloxane microfluidic device that provides for running multiple assays on multiple samples. For example, a 32×32 matrix chip has the capability of running 32 individual assays on 32 individual samples. A 48×48 matrix chip has the capability of running 48 individual assays on 48 individual samples. A 96×96 matrix chip has the capability of running 96 individual assays on 96 individual samples. The 96×96 matrix chip is described in greater detail in co-pending U.S. Provisional App. No. 61/044,417, which is hereby incorporated by reference herein for its description of the design, fabrication, and use of the 96×96 chip.

In exemplary embodiments, 5 to 96 individual PCR assays, particularly from about 5 to 48 assays, more particularly from about 8 to about 48 assays, and even more particularly from about 10 to about 48 assays are carried out to detect amplicons of interest. In other embodiments, greater than 10, greater than 12, greater than 15, greater than 17, greater than 20, greater than 23, greater than 25, greater than 28, greater than 30, greater than 33, greater than 35, greater than 37, greater than 40, greater than 45 greater than 48, greater than 50, greater than 53, greater than 55, greater than 58, greater than 60, greater than 63, greater than 65, greater than 68, greater than 70, greater than 73, greater than 75, greater than 78, greater than 80, greater than 83 greater than 85, greater than 88, greater than 90, greater than 93, or greater than 96 PCR assays are performed from the sample prepared from a single cell. In certain embodiments, particularly in quantitative PCR experiments, the primers in the preamplification mix should be limited, and the number of amplification cycles should be limited, so as to provide for equal amplification of all target nucleic acids of interest.

For running real-time PCR reactions, reaction mixtures generally contain an appropriate buffer, a source of magnesium ions ($Mg^{2+}$) in the range of about 1 to about 10 mM, e.g., in the range of about 2 to about 8 mM, nucleotides, and optionally, detergents, and stabilizers. An example of one suitable buffer is TRIS buffer at a concentration of about 5 mM to about 85 mM, with a concentration of 10 mM to 30 mM preferred. In one embodiment, the TRIS buffer concentration is 20 mM in the reaction mix double-strength (2×) form. The reaction mix can have a pH range of from about 7.5 to about 9.0, with a pH range of about 8.0 to about 8.5 as typical. Concentration of nucleotides can be in the range of about 25 mM to about 1000 mM, typically in the range of about 100 mM to about 800 mM. Examples of dNTP concentrations are 100, 200, 300, 400, 500, 600, 700, and 800 mM. Detergents such as Tween 20, Triton X 100, and Nonidet P40 may also be included in the reaction mixture. Stabilizing agents such as dithiothreitol (DTT, Cleland's reagent) or mercaptoethanol may also be included. In addition, master mixes may optionally contain dUTP as well as uracil DNA glycosylase (uracil-N-glycosylase, UNG). UNG is the product of the *Escherichia coli* ung gene, and has been cloned, sequenced and expressed in *E. coli*. Uracil DNA glycosylase (UDG) removes uracil residues from DNA (single- and double-stranded) without initial destroying the DNA sugar-phosphodiester backbone, thus preventing its use as a hybridization target or as a template for DNA polymerases. The phosphodiester bonds flanking the resulting abasic sites become susceptible to hydrolytic cleavage at elevated temperatures. Thus, removal of uracil bases is usually accompanied by fragmentation of the DNA. Duncan, B. K., and Chambers, J. A. (1984) *GENE* 28, 211, Varshney, U., Hutcheon, T., and van de Sande, J. H. (1988) *J. Biol. Chem.* 263, 7776. A master mix is commercially available from Applied Biosystems, Foster City, Calif., (TaqMan® Universal Master Mix, cat. nos. 4304437, 4318157, and 4326708).

PCR Master Mixes can also contain structure-destabilizing base analogs, such as 7-deazaguanine to prevent Hoogsteen bond formation. A consequence of this is the possibility to carry out structure-independent amplification. See, e.g., U.S. Pat. No. 5,091,310, issued Feb. 25, 2992 to Innis et al.

In a specific aspect, a pre-sample mix may be prepared which may include TaqMan Universal Master Mix, Ampli-Taq-Gold® (about 5 units/µl), 20× GT buffer, and $H_2O$. The pre-sample mix may be combined with the nucleic acid of interest, and appropriate primers.

In one aspect of the invention, a 1× GT buffer may contain betaine in a range of about 0.1 M to about 0.8 M, BSA in a range of about 1 mg/ml to about 4 mg/ml, glycerol in a range of about 1% to about 5%, PEG 20,000 in a range of about 1% to about 5%, PEG MME550 in a range of about 0.05% to about 5%, MME5000 in a range of 1% about to about 5%, Superblock® in PBS in a range of about 1% to about 15%, Superblock® T20 in a range of about 1% to about 10%, and Tween 20 in a range of 0.1% about to about 3%. In a specific aspect, the 1x GT buffer may contain about 0.4 M betaine, 2 mg/ml BSA, about 2.5% glycerol, about 2% PEG 20,000, about 1% PEG MME550, about 2.5% MME5000, about 10% Superblock® in PBS, about 5% Superblock® T20, and about 0.5% Tween 20. In a more specific embodiment, the 1× GT buffer may contain about 0.4 M betaine, 4 mg/ml BSA, about 5% glycerol, about 2% PEG 20,000, about 1% PEG MME550, about 2.5% MME5000, about 10% Superblock® in PBS, about 10% Superblock® T20, and about 1% Tween 20.

In another aspect of the invention, a 20× GT buffer may be prepared and may be diluted to a final concentration of 1× in the reaction mixtures. For example, a 20× GT buffer may include betaine in a range of about 1M to about 10M, BSA in a range of about 5 mg/ml to about 15 mg/ml, and Superblock® T20 (in TBS) in a range of about 20% to about 65%. In a particular aspect, the GT buffer may include about 5 M betaine, about 10 mg/ml BSA, and about 57% Superblock®T20 in TBS. As one skilled in the art appreciates, the 20× GT buffer would be diluted to 1× in the final reaction mix.

In particular embodiments, the assay usually has a dynamic range of at least 3 orders of magnitude, more often at least 4, at least 5, at least 6, at least 7, or at least 8 orders of magnitude.

Detection

Detection of amplicons can be carried out by any means known in the art. Fluorogenic nuclease assays are one specific example of a real-time quantitation method that can be used successfully in the methods described herein. This method of monitoring the formation of amplification product involves the continuous measurement of PCR product accumulation using a dual-labeled fluorogenic oligonucleotide probe--an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties, and specifically for their disclosure of the use of dual-labeled fluorogenic oligonucleotide probes. It will be appreciated that while "TaqMan® probes" are the most widely used for qPCR, the invention is not limited to use of these probes; any suitable probe can be used. In particular embodiments, any detection method in which the probe is a dual-labeled fluorogenic oligonucleotide probe can be used.

In specific embodiments, fluorophores that can be used as detectable labels for probes include, but are not limited to, rhodamine, cyanine 3 (Cy 3), cyanine 5 (Cy 5), fluorescein, Vic™, Liz™., Tamra™, 5-Fam™, 6-Fam™, and Texas Red (Molecular Probes). (Vic™, Liz™., Tamra™, 5-Fam™, 6-Fam™ are all available from Applied Biosystems, Foster City, Calif.).

In some embodiments, the amount of labeling probe that gives a fluorescent signal in response to an excitation light typically relates to the amount of nucleic acid produced in the amplification reaction. Thus, in such embodiments, the amount of fluorescent signal is related to the amount of product created in the amplification reaction. In such embodiments, one can therefore measure the amount of amplification product by measuring the intensity of the fluorescent signal from a fluorescent indicator. According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in "real-time." In certain embodiments, one can use the amount of amplification product and number of amplification cycles to calculate how much of the target nucleic acid sequence was in the sample prior to amplification.

According to some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid.

By acquiring fluorescence over different temperatures, it is possible to follow the extent of hybridization. Moreover, the temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6472156; and 6,569,627, each of which is hereby incorporated by reference in its entirety, and specifically for its description of the use of melting curve analysis to detect and/or quantify amplification products. In illustrative embodiments, melting curve analysis is carried out using a double-stranded DNA dye, such as SYBR Green, Eva Green, Pico Green (Molecular Probes, Inc., Eugene, Oreg.), ethidium bromide, and the like (see Zhu et al., 1994, Anal. Chem. 66:1941-48).

Labeling Strategies

Any suitable labeling strategy can be employed in the methods described herein. Where the amplification mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Eva Green, or Pico Green, or sequence-specific probes that bind to a nucleotide sequence present in all amplification products. Binding sites for sequence-specific probes can be conveniently introduced into the target nucleic acids during preamplification and/or during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 5-, 10-, 20-, 50-, 100-fold (or to any degree in a ranged defined by any of these values) prior to amplification to improve the specificity of the subsequent amplification step.

In some embodiments, undesired components can be removed by a variety of enzymatic means. Examples of suitable enzymatic means include enzymes that digest single-stranded nucleic acids, such as *E. coli* exonuclease I. Excess dNTPs left over from the amplification reaction can be "removed" by treatment with shrimp alkaline phosphatase (SAP), which removes the phosphate groups from dNTPs. Uracil N-glycosylase (UNG) (AmpErase® from Applied Biosystems, Inc., Foster City, Calif.) can be used to prevent unwanted carry-over of primers from an initial amplification reaction in which the primers contained dUTP, instead of dTTP. UNG degrades U-containing primers.

Alternatively, unreacted primers and dNTPs can be removed by column chromatography. For example, gel filtration via Sephadex can be employed for this purpose.

In particular embodiments, clean-up includes selective immobilization of nucleic acids. For example, desired nucleic acids can be preferentially immobilized on a solid support. In an exemplary embodiment, photo-biotin is attached to desired nucleic acid, and the resulting biotin-labeled nucleic acids immobilized on a solid support comprising an affinity-moiety binder such as streptavidin. Alternatively, unwanted nucleic acids can be immobilized on a solid support and desired nucleic acids harvested by washing.

Applications

The methods described herein are applicable to any technique aimed at detecting the presence or amount of one or more target nucleic acids in a nucleic acid sample. Thus, for example, these methods are applicable to identifying the presence of particular polymorphisms (such as SNPs), alleles, or haplotypes, or chromosomal abnormalities, such as amplifications, deletions, or aneuploidy. The methods may be employed in genotyping, which can be carried out in a number of contexts, including diagnosis of genetic diseases or disorders, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods described herein can be applied to the identification of sequences indicative of particular conditions or organisms in biological or environmental samples. For example, the methods can be used to identify pathogens, such as viruses, bacteria, and fungi). The methods can also be used to characterize environments or microenvironments, e.g., to characterize the microbial species in the human gut.

These methods can also be employed to determine DNA or RNA (e.g., mRNA, miRNA) copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

Kits

Kits according to the invention can include one or more reagents useful for practicing one or more assay methods described herein. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

Protocol for Preamplification and Amplification of Samples Produced by Whole Genome Amplification of a Single Cell DNA from single cells was amplified by whole genome amplification, followed by preamplification and then loading on a Fluidigm matrix chip and analyzed by quantitative real-time polymerase chain reaction (qPCR) using the BioMark™ system. The preamplification and on-chip amplification were carried out in the following manner.

A preliminary amplification was performed to obtain the preamplified sample from a single cell. The preliminary amplification was performed by combining 2.5 µl of single-cell sample with buffer (after Whole Genome Amplification), 2.5 µl of pooled assays containing 192 assays at 180 nMol of forward primers and reverse primers each and 50 nMol of probe and 5 µl of 2× TaqMan® PreAmp Master Mix (Applied Biosystems, Foster City, Calif.). This reaction was performed by 95° C. for 10 min, followed by 14 cycles of 15 sec at 95° C. and 4 min at 60° C.

The amplifications were performed in a Fluidigm Dynamic Array chip. The solutions added to the assay inlets of the 96.96 array (Fluidigm Corporation, South San Francisco, Calif.) consisted of the primer at a concentration of 9 µM and the probe at a concentration of 2.5 µM, 1 µl, 50× ROX (Invitrogen) and 0.25% Tween 20. The solution added to the sample inlets was prepared by mixing 2.5 of the preamplified sample, 3 µL 2× TaqMan® Universal Master Mix (Applied Biosystems, Foster City, Calif.), 0.1 µl AmpliTaq Gold Polymerase (Applied Biosystems, Foster City, Calif.), 0.3 µL 20× GT Sample Loading Buffer (Fluidigm Corporation, South San Francisco) and 0.1 µl DNA-free water. After loading using the NanoFlex™ IFC Controller (Fluidigm Corporation, South San Francisco), PCR and fluorescence detection were performed in the BioMark™ System (Fluidigm Corporation, South San Francisco, Calif.) for genetic analysis. The thermal cycling protocol consisted of 50° C. for 2 min, 70° C. for 30 min, 25° C. for 10 min, 50° C. for 2 min, 95° C. for 10 min followed by 40 cycles of 15 sec at 95° C. and 1 min at 60° C. The final concentrations in the reaction chambers of the array were 900 nM each forward and reverse primer and 250 nM probe.

Example 2

Methods and Protocols to Detect Messenger RNA, MicroRNAs, or Small RNA Species Using Fluidigm Microfluidic Devices and Single-cell Amounts of Nucleic Acids This Example describes methodologies required for obtaining kinetic amplicon "real-time" detection of messenger (mRNA), microRNA (miRNA), and/or other small RNA species and using 48.48 or 96.96 Dynamic Array Integrated Fluidic Circuit (IFC)s using low quantity nucleic acid samples. This Example focuses on examining these nucleic acids when derived from small numbers of cells or single cells. Using a 48.48 Dynamic Array™ IFC it is possible to analyze up to 48 targets for 48 individual samples. Using a 96.96 Dynamic Array™ IFC it is possible to analyze up to 96 targets for 96 individual samples. The associated protocols can be adapted to analyze even more samples/and or target on a 48 or 96 chip, as described in copending U.S. Ser. No. 12/548,132, filed Aug. 26, 2006, which is hereby incorporated by reference for all purposes and in particular for its description of methods for tagging samples and/or target assays for multiplex analysis.

A) Detection of mRNA

An exemplary protocol entails analyzing single-cell gene expression using the BioMark 48.48 Dynamic Array and real-time PCR. This protocol is described below as a new and efficient method for obtaining gene expression data for up to 48 genes from a single cell, using the BioMark™ and 48.48 IFCs. This protocol enables examination of the contents of a cell with minimal sample preparation time and expense. This protocol covers the laboratory procedure and reagent requirements for performing single-cell gene expression studies using the Invitrogen CellsDirect™ One-Step qRT-PCR kit (Catalog numbers, 11753-100 and 11753-500) and the specific target amplification (STA) procedure. This approach combines reverse transcription and specific target amplification of single-cell assays. This approach can be adapted to analyze any nucleic acid target and in useful for analyzing poor quality samples, as well as single-cell samples.

Reagents for analysis of mRNA species in single cells
    CellsDirect™ One-Step qRT-PCR kit (Invitrogen, catalog numbers, 11753-100 and 11753-500)
    Optional: SUPERase-In™ (Ambion, PN AM2694)
    TaqMan® Universal PCR Master Mix (Applied Biosystems, PN 4304437)
    TE buffer (Technova)
    Single-step RT-STA (preamplification) for single-cell experiments 1. Users can start by employing 20× stock assays (including primers) as described in Fluidigm's STA Quick Reference Card (PN 68000133RevB).
2. Pool all real-time assays and dilute with TE buffer so that each assay is at a final concentration of 0.2×. This is the 0.2× Assay Mix.
3. Prepare the sample RT-STA Master Mix by combining the following components:

| Component | Volume (µl) |
| --- | --- |
| CellsDirect 2x Reaction Mix | 5.0 |
| 0.2x Assay Mix | 2.5 |
| SuperScript ™ III RT/Platinum ® Taq Mix | 0.2 |
| TE buffer | 1.3 |
| Total | 9 |

NOTE: If cells are to be stored prior to RT-STA or if RNase activity is suspected, add 0.1 μL of Ambion's SUPERaseIn to the RT-STA Master Mix.

4. Aliquot 9 μl of RT-STA Master Mix to each tube or reaction well of a multi-well plate. Sort cells by fluorescence-activated cell sorting (FACS) into each individual tube or reaction well. (These steps can be varied depending on researchers' needs).
5. Tap the tube or plate to mix.
6. Use immediately or store at −20° C.
   Comment# 1: The volume can be reduced to 5 μl if cell sorting can be accomplished with that reaction volume.
   Comment# 2: Probe use during STA is optional unless unavoidable because the probe is also present in a prepared assay mix. Probe can be omitted when performing high numbers of STA with low starting numbers of molecules. Omitting probe at this step may result in more robust baseline subtraction.
   Comment #3: The single cell-containing reaction mix can be transferred to a thermal cycler for immediate RT/STA thermal cycling.
7. Reverse transcribe the RNA to cDNA at 50° C. for 15 minutes.
8. Inactivate the RT enzyme, and activate the Taq by bringing the sample to 95° C. for 2 minutes.
9. Specific target amplify (STA) the cDNA for 18 cycles of: 95° C. for 15 seconds; 60° C. for 4 minutes.
10. Dilute the resulting preamplified cDNA product 1:5 with TE buffer.

Detection by Real-time PCR (Amplification)
1. Prepare the real-time reaction mixtures according to the table below.:

| Component | Volume (μl) |
| --- | --- |
| 2x TaqMan ® Universal PCR Master Mix | 2.5 |
| Fluidigm Sample Loading Reagent | 0.25 |
| Preamplified cDNA | 2.25 |
| Total | 5 |

2. Vortex and then pipette the real-time reaction mix into the sample inlets of a Fluidigm Dynamic Array (DA).
3. Pipette 10× assays into the assay inlets on the DA.
4. Follow the BioMark Real-Time PCR Analysis Software Quick Reference Card (PN 68000089) for complete running instructions for real-time experiments.

B) Detection of MicroRNA and/or Small RNA

A separate exemplary protocol entails analyzing micro RNA in single cells using the BioMark 48.48 Dynamic Array and real-time PCR (PN 100-1616 A1). This protocol permits examination of miRNAs from low concentrations of total nucleic acid. Both miRNAs and small RNA species (U6) can be examined. This protocol describes the laboratory procedures and reagent requirements for analyzing miRNAs and/or small RNAs from as little as 100 picograms of total RNA (~10 cells) after 15-18 specific target amplification (STA) cycles. In this example, the protocol utilizes the MegaPlex™ Pools for both reverse transcription (RT) and specific target amplification (STA) from Applied Biosystems. MegaPlex™ A and B pools each include up to 381 unique primer pairs, making it possible to use the same sample to analyze many different miRNAs with minimal sample input.

Reagents for Analysis of miRNA Species
CellsDirect™ One-Step qRT-PCR kit (Invitrogen, catalog numbers, 11753-100 and 11753-500)
Optional: SUPERase-In™ (Ambion, PN AM2694)
TaqMan® Universal PCR Master Mix (Applied Biosystems, PN 4304437)
TE buffer (Technova)

Preparing the Megaplex (RT) Reaction Mix and Reverse Transcription of RNA
1. Prepare the RT reaction mix in a 1.5 mL micro centrifuge tube according to the following table:

| RT Reagent Mix Components | Volume for One Reaction (μl) | Volume for 60 Reactions (μl) |
| --- | --- | --- |
| MegaPlex RT Primers (10X) | 0.80 | 48 |
| dNTPs with dTTP (100 mM) | 0.20 | 12 |
| MultiScribe Reverse Transcriptase (50 U/μL) | 1.50 | 90 |
| 10X RT buffer | 0.80 | 48 |
| MgCl$_2$ (25 mM) | 0.90 | 54 |
| RNase Inhibitor (20 U/μL) | 0.10 | 6 |
| Nuclease-Free Water | 0.20 | 12 |
| Total | 4.50 | 270 |

2. Vortex the tube gently several times to mix thoroughly; centrifuge briefly to collect contents.
3. Aliquot 4.5 μL of the RT reaction mix into each reaction well of a multi-well plate.
4. Add 3.5 μL (100 pg to 350 ng) total RNA into each well containing reaction mix.
5. Vortex and centrifuge.
6. Incubate the plate on ice for 5 minutes.
7. Thermal cycle the reaction as described in the table below:

| Stage | Temperature | Time | Cycles |
| --- | --- | --- | --- |
| Anneal | 16° C. | 2 min | 1 |
| Extend | 42° C. | 1 min | 40 |
|  | 50° C. | 1 sec | 40 |
| Enzyme inactivation | 85° C. | 5 min | 1 |
| Hold | 4° C. | hold | — |

Comment: The cDNA can be stored at −15° C. to −25° C. for at least one week.

Specific Target Amplification (Also Known as Preamplification)
1. Prepare the STA reaction mix in a 1.5 mL microcentrifuge tube according to the following table:

| STA Reaction Mix Components | Volume for One Reaction (μL) | Volume for 60 reactions (μL) |
| --- | --- | --- |
| 2X TaqMan ® PreAmp Master Mix | 2.5 | 150 |
| 10X MegaPlex ™ PreAmp Primers | 0.5 | 30 |
| Total | 3.0 | 180 |

2. Vortex and centrifuge STA reaction mix.
3. Aliquot 3 μL of the STA reaction mix to each reaction well of a multi-well plate.
4. Add 2 μL of reversed transcribe RNA from above to each reaction.
5. Vortex the reaction plate and spin down.
6. Incubate the plate on ice for 5 minutes.
7. Run the STA protocol according to the table below:

| Stage | Temperature | Time | Cycles |
|---|---|---|---|
| Hot Start | 95° C. | 10 min | 1 |
| Anneal | 55° C. | 2 min | 1 |
| Extend | 72° C. | 2 min | 1 |
| Denature | 95° C. | 15 sec | 15-to-18 |
| Anneal/Exten | 60° C. | 4 min | 15-to-18 |
| Hold | 99.9° C. | 10 min | 1 |
| Hold | 4° C. | hold | 1 |

Figure 3:
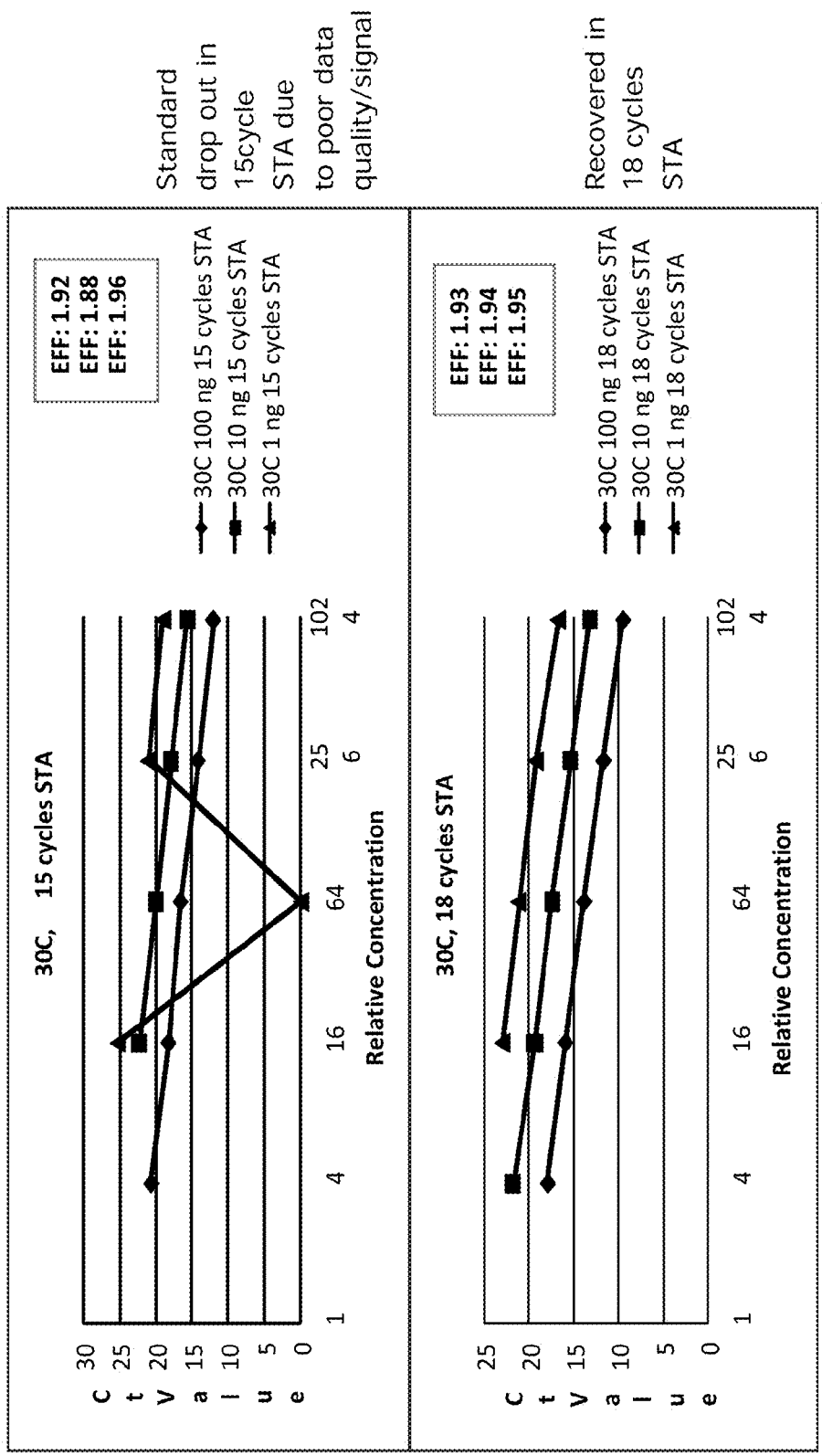
FIG. 3: miRNA 30C assay linearity "standard curve" generated from specific target amplified (STA) template derived from various starting levels of total RNA, analyzed as described in Example 2B. Data is expressed in terms of Ct versus relative concentration. EFF indicates PCR efficiency over the dilution series.
Figure 4:
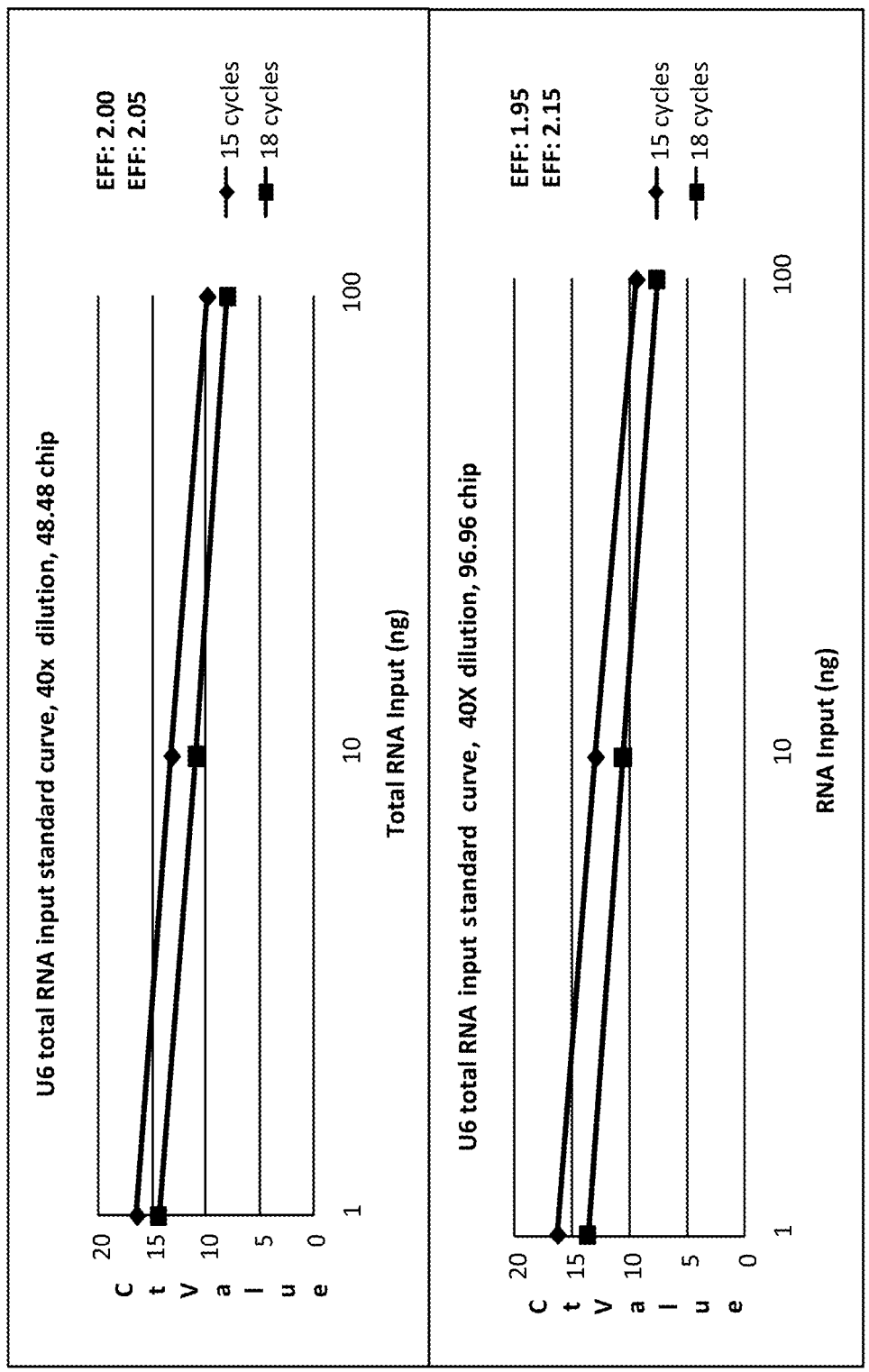
FIG. 4: Standard curves of U6 assay linearity taken from the same STA dilution, but from different starting amounts of total RNA, analyzed as described in Example 2B. Assays demonstrate remarkable response linearity from the reverse transcription (RT) step through the STA and finally in the Integrated Fluidic Circuit (IFC). Data is expressed in terms of Ct value versus ng of total RNA input. EFF indicates PCR efficiency over the dilution series.
Figure 5:
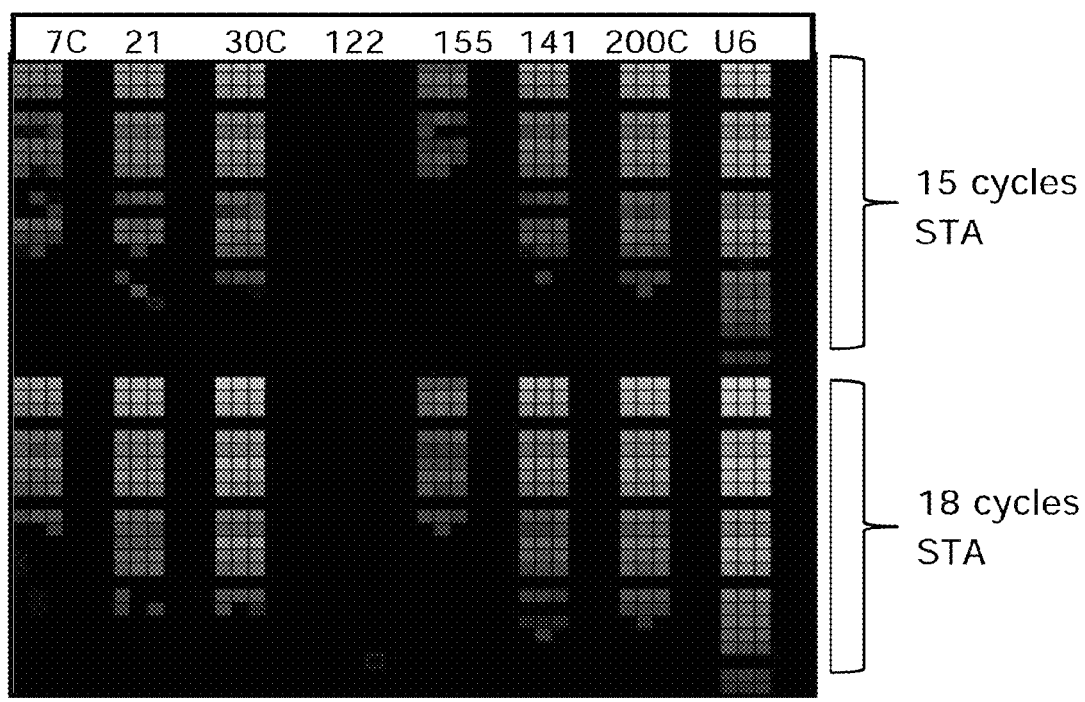
FIG. 5: A 48.48 Ct heat map of miRNA expression data (Example 2B). Data was derived using differing input amounts of total RNA. STA for 15 or 18 cycles.
Figure 6:
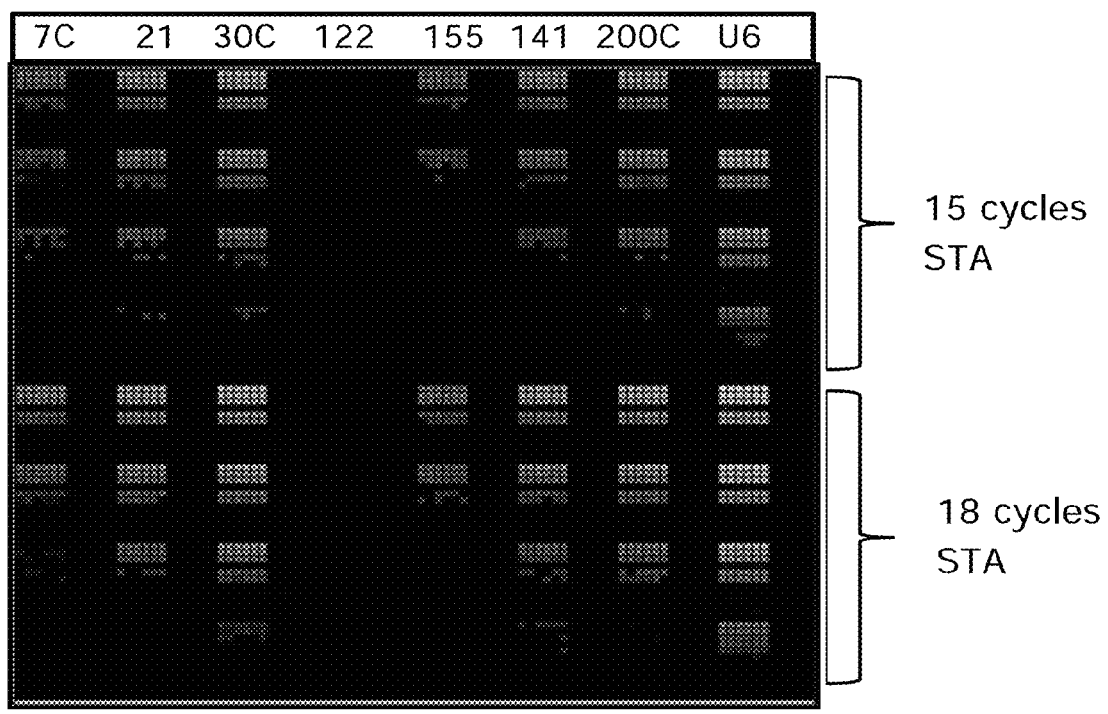
FIG. 6: A 96.96 Ct heat map of miRNA expression data. Data was derived using differing input amounts of total RNA. STA for 15 or 18 cycles.

8. Dilute template ~1:10 by adding 45 µl of Low EDTA TE buffer to each reaction, for a final volume of 50 µl
   Comment: STA cycle numbers are a recommendation only. The optimal number of STA cycles to be performed will need to be empirically determined, and is dependent on miRNA abundance in each sample.
   Detection by Real-time PCR (Amplification)
   Refer to the Fluidigm 48.48 Real-Time PCR Workflow Quick Reference Card (PN 68000089) or the Fluidigm 96.96 Real-Time PCR Workflow Quick Reference Card (PN 68000130) for complete instructions on preparing Assays and Samples for analysis.
   When running a 48.48 Dynamic Array IFC: If Pool A RT Primers and STA Primers have been used, then up to 48 individual TaqMan MicroRNA assays from Pool A can be selected for running on the DA. If Pool B RT Primers and STA Primers have been used, then up to 48 individual TaqMan MicroRNA assays from Pool B can be selected for running on the DA.
   When running a 96.96 Dynamic Array IFC: If Pool A RT Primers and STA Primers have been used, then up to 96 individual TaqMan MicroRNA assays from Pool A can be selected for running the DA. If Pool B RT Primers and STA Primers have been used, then up to 96 individual TaqMan MicroRNA assays from Pool B can be selected for running on the DA.
   Results
   Typical miRNA expression data (miRNA 30C, FIG. 3 or control small RNA U6, FIG. 4) were obtained using a Fluidigm DA. miRNA or small RNA concentration were measured using varying inputs of total RNA after STA for differing numbers of cycles. EFF indicates PCR efficiency over the dilution series. FIGS. 5 and 6 below display Ct heat maps of data derived using m48 and m96 DAs.
   FIG. 3 shows standard curves generated from STA amplified template from various starting levels of total RNA. The dilutions for the standards were performed after the STA reaction, to demonstrate linearity observed with dynamic array PCR. This linearity is maintained from varying levels of starting material.
   FIG. 4 shows standard curves derived from the same STA dilution, but from different starting amounts of total RNA, demonstrating remarkable assay linearity from the RT step through the STA and finally in the dynamic array PCR.

C) Protocol/Methodology Variations
1. Variations in the sample amount and reagent volumes.
2. Increasing the number of STA thermal cycles, up to 24 cycles.
3. Removing probe from the STA reactions to ameliorate accumulation of baseline fluorescence.
4. Alternate kinetic amplicon detection methods employing DNA binding dyes such as SYBR Green or Eva Green.
5. Use of non-STA (i.e., non-preamplified) material. An illustrative non-STA approach can include, e.g., polyadenylation of all non-rRNA prior to Eberwine-style run-off transcription. More specifically, some portion of the transcripts in total RNA do not necessarily contain poly-A tails; therefore, they will be excluded by a poly-A RNA-positive selection technique, unless poly-A tails are added. An rRNA reduction approach can make the protocol more robust in handling smaller amounts of total RNA samples. In an illustrative protocol, four biotinylated LNA RiboMinus probes are designed to specifically bind to the abundant 18S and 28S rRNA species (2 probes each for 18S and 28S rRNA). Following hybridization of the biotinylated probes to the rRNA molecules in the total RNA sample, the rRNA is efficiently removed from the sample by the addition of the RiboMinus Magnetic Beads that are coated with streptavidin. This process is commonly used by Affymetrix Corp. See. www.affymetrix.com/support/help/faqs/wt . . . /faq_1.jsp. Kits to perform this process are available from Invitrogen (RiboMinus™ Technology).
6. Use of locked nucleic acid bearing primers or other primers bearing modified nucleotides or phosphodiester bonds (i.e. Exiqon-type approach). In this case, preamplification may not be required.
7. Use of alternate single cell lysis methods including use of CelluLyser Lysis and cDNA Synthesis Kits (available from TATAA Biocenter AB, Odinsgatan 28411 03 Göteborg, Sweden) to facilitate denaturation of RNA and potentiate enhanced reverse transcription.

What is claimed is:
1. A method for analyzing DNA from a single cell, said method comprising:
   (a) performing whole genome amplification of the genome of a single cell to produce an amplified genome, wherein the method entails performing whole genome amplification for fewer than, or about, 10 amplification cycles;
   (b) preamplifying the amplified genome using a plurality of target-specific primer pairs to produce a preamplification reaction mixture comprising a plurality of amplicons specific for a plurality of target nucleic acids;
   (c) distributing the plurality of amplicons within a device; and
   (d) amplifying and detecting the plurality of amplicons in the device.
2. A method for analyzing mRNA from a single cell, said method comprising:
   (a) preparing DNA from the mRNA of a single cell;
   (b) preamplifying the DNA using a plurality of target-specific primer pairs to produce a preamplification reaction mixture comprising a plurality of amplicons specific for a plurality of target nucleic acids, wherein said preamplification is carried out for 18 amplification cycles or fewer;
   (c) distributing the plurality of amplicons within a device; and
   (d) amplifying and detecting the plurality of amplicons in the device.
3. A method for analyzing non-coding RNA from a single cell, said method comprising:
   (a) preparing DNA from the non-coding RNA of a single cell;
   (b) preamplifying the DNA using a plurality of target-specific primer pairs to produce a preamplification reaction mixture comprising a plurality of amplicons specific for one or more target nucleic acids;
   (c) distributing the plurality of amplicons within a device; and
   (d) amplifying and detecting the plurality of amplicons in the device.
4. A method for analyzing DNA from a single cell, said method comprising:

(a) performing whole genome amplification of the genome of a single cell to produce an amplified genome, wherein the whole genome amplification comprises polymerase chain reaction (PCR) cycles;

(b) preamplifying the amplified genome using a plurality of target-specific primer pairs to produce a preamplification reaction mixture comprising a plurality of amplicons specific for one or more target nucleic acids;

(c) distributing the plurality of amplicons within a device; and (d) amplifying and detecting the plurality of amplicons in the device.

5. A method for analyzing RNA from a single cell, said method comprising:

(a) preparing DNA from the RNA of a single cell;

(b) preamplifying the DNA using a plurality of target-specific primer pairs to produce a preamplification reaction mixture comprising a plurality of amplicons specific for one or more target nucleic acids;

(c) distributing the plurality of amplicons within a device; and (d) amplifying and detecting the plurality of amplicons in the device.

6. The method of any of claim 1, 2, or 3-5, wherein said single cell comprises a mammalian cell.

7. The method of claim 6, wherein said single cell is selected from a cell from a preimplantation embryo, a stem cell, a suspected cancer cell, a cell from a pathogenic organism, and a cell obtained from a crime scene.

8. The method of claim 7, wherein the cell comprises a human blastomere.

9. The method of claim 8, wherein the human blastomere is from an eight-cell stage embryo.

10. The method of claim 7, wherein the cell comprises a human stem cell.

11. The method of claim 4, wherein said whole genome amplification is carried out such that a reaction plateau is not reached.

12. The method of claim 1 or 4, wherein said whole genome amplification is performed for more than two amplification cycles.

13. The method of claim 4, wherein said whole genome amplification is performed for fewer than, or about, 10 amplification cycles.

14. The method of claim 12, wherein said whole genome amplification is performed for between four and eight cycles, inclusive.

15. The method of claim 1 or 4, wherein said whole genome amplification is carried out using a technique selected from the group consisting of primer extension PCR (PEP), degenerated oligonucleotide primed PCR, ligation-mediated PCR (LMP), the T7-based linear amplification of DNA (TLAD), and multiple displacement amplification (MDA).

16. The method of claim 2, wherein the DNA is cDNA produced by reverse transcription of mRNA.

17. The method of claim 5, wherein the RNA comprises non-coding RNA.

18. The method of claim 17 or 3, wherein the non-coding RNA is selected from the group consisting of small nucleolar RNA (snoRNA), microRNA (miRNA), small interfering RNA (siRNA), and Piwi-interacting RNAs (piRNA).

19. The method of claim 17 or 3, wherein DNA is produced from the non-coding RNA by reverse transcription or amplification.

20. The method of claim 1 or 5, wherein said preamplification is carried out for 8-18 cycles.

21. The method of any of claim 1, 2, or 3-5, wherein said amplification is carried out using one or more primer pairs specific for said one or more target nucleic acids.

22. The method of claim 16, wherein DNA is produced by reverse transcription, which is followed by preamplification in the same reaction mixture.

23. The method of claim 16, wherein no probe is present in the preamplification mixture.

24. The method of claim 1, 2, or 3-5, wherein said plurality of target-specific primer pairs used for preamplification amplifies one or more single nucleotide polymorphisms (SNPs).

25. The method of claim 24, wherein the presence of said one or more SNPs is/are correlated with the presence of one or more genetic defects.

26. The method of any of claim 1, 2, or 3-5, wherein the device comprises a microfluidic device is fabricated, at least in part, from an elastomeric material.

27. The method of any of claim 1, 2, or 3-5, wherein the preamplification and the amplification is carried out by polymerase chain reaction (PCR).

28. The method of any of claim 1, 2, or 3-5, wherein the presence of an amplification product is determined by quantitative real-time polymerase chain reaction (qPCR).

29. The method of claim 28, wherein a universal qPCR probe is employed in the amplification mixtures to detect amplification products.

30. The method of claim 29, wherein the universal qPCR probe comprises a double-stranded DNA (dsDNA) dye.

31. The method of claim 28, wherein one or more target-specific qPCR probes is employed in the amplification mixtures to detect amplification products.

32. The method of claim 28, wherein the presence of an amplification product is detected using a fluorogenic nuclease assay.

33. The assay method of claim 32, wherein the presence of an amplification product is detected using a dual-labeled fluorogenic oligonucleotide probe.

34. The method of any of claim 1, 2, or 3-5, wherein the plurality of amplicons comprises at least 10 amplicons.

35. The method of any of claim 1, 2, or 3-5, wherein the plurality of amplicons comprises from 10 to 96 amplicons.

* * * * *